United States Patent [19]

Lok

[11] Patent Number: 5,753,462
[45] Date of Patent: May 19, 1998

[54] SECRETION LEADER TRAP CLONING METHOD

[75] Inventor: Si Lok, Seattle, Wash.

[73] Assignee: Zymogenetics, Inc., Seattle, Wash.

[21] Appl. No.: 796,508

[22] Filed: Feb. 6, 1997

Related U.S. Application Data

[63] Continuation of Ser. No. 472,806, Jun. 7, 1995, abandoned.

[51] Int. Cl.⁶ .................. C12N 15/66; C12N 15/11; C12P 21/02
[52] U.S. Cl. .................. 435/69.1; 435/172.3; 536/23.1
[58] Field of Search .................. 435/69.1, 172.3; 536/23.1

[56] References Cited

U.S. PATENT DOCUMENTS 5,536,637  7/1996  Jacobs .................................. 435/6

FOREIGN PATENT DOCUMENTS

| 0244042 | 4/1987 | European Pat. Off. |
| 0607054 | 1/1994 | European Pat. Off. |
| 0645449 | 9/1994 | European Pat. Off. |
| 3901681 | 7/1990 | Germany |
| 8912063 | 12/1989 | WIPO |
| 9107505 | 5/1991 | WIPO |

OTHER PUBLICATIONS

Tashiro et al. Science 261 600–602 (1993) Signal sequence Trap: a cloning strategy for secreted proteins . . . .
Chodosh et al. Mol. and Cell. Biology 6 4723–4733 (1986) A single polypeptide posseses the binding and transcription activities . . . IBI Catolog 1990 pp. 26–38 Restriction Enzymes.
Olsuik et al. Clin. Microbiol. Rev. 7 43–54 (1994) Magnetic Separation Techniques in diagnostic microbiology.
Skoda et al. Embo J. 12 2645–2653 (1993) Murine c–mpl: a member of the hematopoietic growth . . . .
Lok et al. Gene 140 203–209 (1994) The human glucagon receptor encoding gene: structure cDNA . . . .
Blanco et al. Molecular Microbiology 5 2405–2415 (1991) Identification of Treponema pallidum subspecies pallidum . . .
J. Edwards et al., Oligodeoxyribonucleotide ligation to single–stranded cDNAs: a new tool for cloning 5' ends of mRNAs and for constructing cDNA libraries by in vitro amplification. *Nucleic Acids Research* 19:19, 5227–5232, 1991.
W. M. Bertling et al., Determination of 5' Ends of Specific mRNAs by DNA Ligase–dependent Amplification. *PCT Methods and Applications* 2: 95–99, 1993.
T. Ward et al., Decay–accelerating factor CD55 is identified as the receptor for echovirus 7 using CELICS. A rapid immuno–focal cloning method. *EMBO Journal* 13:21, 5070–5074, 1994.
Edery et al., *Mol. Cell. Biol.* 15(6):3363–3371, 1995.
Rice et al., *Proc. Natl. Acad. Sci. USA 89:* 5467–5471, 1992.

Primary Examiner—James Ketter
Assistant Examiner—John S. Brusca
Attorney, Agent, or Firm—Ann W. Speckman; Janet Sleath

[57] ABSTRACT

Expression vectors and methods for cloning amino-terminal signal sequences are disclosed. These vectors and methods are useful tools for cloning, identifying and isolating previously unknown signal sequences. In turn, an orphan signal sequence can be used to clone, identify and isolate the corresponding orphan proteins that the orphan signal sequence directs to the surface of a cell. Using these expression vectors and methods, an orphan protein can be cloned in the absence of a functional assay that detects such protein.

22 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GAGGAGAAGG TCGACTCAAG GCTGCTGCCA ATAGCTTAG     39

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GAGGAGCTCG AGGGTCAAGA TGTCTTCTTG CTGGCCTT     38

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GAGGAGCTCG AGTCAAGATG TCTTCTTGCT GGCCTT     36

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GAGGAGCTCG AGGTCAAGAT GTCTTCTTGC TGGCCTT     37

SECRETION LEADER TRAP CLONING METHOD

This is a file wrapper continuation patent application of prior application Ser. No. 08/472,806, filed on Jun. 7, 1995, now abandoned.

TECHNICAL FIELD

The invention relates to vectors and methods for cloning amino-terminal signal sequences. With identification of novel signal sequences, previously unidentified secreted and transmembrane proteins, especially those involved in signal transduction, can be identified.

BACKGROUND OF THE INVENTION

A large proportion of secreted proteins function as signal molecules, such as growth factors or cell surface receptors. In general, 1–5% of cellular proteins are secreted proteins. Growth factors are diffusable molecules that mediate intercellular communication. Growth factors include the interleukins, platelet-derived growth factor (PDGF), epidermal growth factor (EGF), granulocyte-macrophage colony stimulating factor (GM-CSF), erythropoietin (EPO), thrombopoietin (TPO) and calcitonin. Receptors include integral membrane proteins and soluble receptors.

A common feature of these molecules of interest is the presence of a secretion leader ("signal") sequence at the N-terminus of their coding regions. This signal sequence encodes amino acids that direct the de novo synthesized protein into the endoplasmic reticulum or to the exterior of the cell. Because the nucleotide homology of known signal sequences is minimal or non-existent, isolation of novel signal sequences by nucleic acid hybridization is difficult, if not impossible.

One method for selective cloning of signal sequences ("signal trapping") has been described by K. Tashiro et al., Science 261:600–03, 1993. This method featured a cDNA library containing cDNA of 400 bp average size. To generated cDNAs of 400 bp average size, the cDNA was sonicated, creating random shear of the cDNA molecules. The randomly sheared cDNA was inserted into a vector (lacking an endogenous signal sequence) capable of directing cell surface expression of Tac fusion protein, if a signal sequence was inserted in-frame in correct orientation. The presence of cell surface Tac fusion protein was microscopically detected by immunostaining with anti-Tac antibodies. After several cycles of subpooling and fluorescent microscopy detection, 6 immunologically positive cDNA clones were obtained from 600 screened clones. From these 6 clones, two new members of the intercrine a cytokine family were identified.

The signal trap cloning method of Tashiro et al. includes the following attendant disadvantages: (1) uncontrolled, non-directional generation of small cDNA fragments through random shear; (2) cumbersome cycles of immunostaining and subpooling of individual clones; and (3) absence of any selection feature in the cloning scheme. The methods of the present invention overcome these disadvantages, and further provide generalized and improved approaches for secretion leader trap cloning.

SUMMARY OF THE INVENTION

It is an object of the present invention to provide methods for selecting 5' terminal DNA fragments comprising: preparing a plurality of DNA molecules having 5' ends, wherein the 5' ends are linked to a first member of a complementary/anti-complementary pair, thereby forming labeled 5' ends; cleaving the DNA molecules with a restriction endonuclease, thereby forming DNA fragments; exposing the DNA fragments to an opposite member of the complementary/anti-complementary pair, whereby DNA fragments having labeled 5' ends are bound to the opposite member; and isolating DNA fragments from the complementary/anti-complementary pair.

It is a further object of the present invention to provide expression vectors comprising the following operably linked elements: a transcription promoter; a first DNA segment encoding a cloning site for insertion of a 5' terminal DNA fragment; a second DNA segment encoding a leader-less protein, whereby in-frame joining of the second DNA segment with the first DNA segment provides cell surface expression of the leader-less protein if a functional signal sequence is inserted in the cloning site; and a transcription terminator.

Within one aspect of the invention, the complementary/anti-complementary pair is selected from the group consisting of a biotin/avidin pair, a receptor/ligand pair, an antibody/epitope pair, and a sense/antisense polynucleotide pair, with a biotin/avidin pair preferred. It is also preferred that one member of the complementary/anti-complementary pair is immobilized on a solid phase matrix, such as a magnetic bead. In another preferred embodiment, the restriction endonuclease is a 4-cutter restriction enzyme.

Within another aspect of the invention, the methods further comprise, after the step of isolating DNA fragments, the additional steps of: joining the DNA fragments to a DNA segment encoding a structural protein, thereby forming a DNA fusion, wherein the DNA fusion is contained within an expression vector and operably linked to other DNA elements required for expression of the DNA fusion in a host cell; introducing the expression vector into a host cell, thereby forming an expression host cell; and culturing the expression host cell, whereby the DNA fusion is capable of being expressed.

In a preferred embodiment, the structural protein is a growth factor receptor, and preferably Mpl. In another preferred embodiment, the expression vector is pSLSV-1, pSLSV-2, pSLSV-3 or combinations thereof. In another preferred embodiment, the host cell is BaF3, a Chinese hamster ovary cell, a baby hamster kidney cell, FDC-P1, or MO7e, with BaF3 cells preferred.

Within yet another aspect of the invention, the methods further comprise, after the step of culturing the expression host cell, the additional steps of: combining the expression host cell with a tagged reagent under conditions whereby the expression host cell is intact and the tagged reagent binds to the structural protein encoded by the DNA segment; and isolating expression host cells that bind the tagged reagent.

In a preferred embodiment, the tagged reagent is a fluorescent-labeled antibody, and the step of isolating is performed using a fluorescence-activated cell sorter. In another preferred embodiment, the host cell is a factor-dependent host cell, preferably BaF3, FDC-P1, or MO7e, and most preferably BaF3. In yet another preferred embodiment, the structural protein is directed to an exterior surface of the expression host cell and is a member of a complementary/anti-complementary pair, whereby interaction of the structural protein with an opposite member of the complementary/anti-complementary pair stimulates the expression host cell bearing the structural protein to proliferate.

In a preferred embodiment, the complementary/anti-complementary pair is a receptor/ligand pair. In another preferred embodiment, the structural protein is Mpl, IL-4 receptor, EPO receptor, or GM-CSF receptor. In yet another preferred embodiment, the step of culturing is conducted in the absence of a factor that the factor-dependent host cell requires for growth, and in the presence of the opposite member of the complementary/anti-complementary pair.

Within a further aspect of the invention, the cloning site is SEQ ID NO: 2; SEQ ID NO: 3; or SEQ ID NO: 4. In another aspect of the invention, the leader-less protein is leader-less Mpl.

These and other aspects of the invention will become evident upon reference to the following detailed description.

DETAILED DESCRIPTION OF THE INVENTION

The present invention combines the secretory function of a signal peptide with functional cloning methods to provide improved methods of identifying and cloning previously unknown signal peptides. By correctly linking a putative signal sequence to a sequence encoding a marker, detectable protein, extracellular expression of such marker protein can be detected.

The secretion leader trap cloning methods and vectors of the present invention can be advantageously used to clone, identify, and isolate cDNA segments encoding previously unknown factors (such as novel cytokines and growth factors) and previously unknown transmembrane molecules (such as novel receptors) which pass through a cell's secretory pathway. Previously unknown factors and receptors are also referred to as "orphan" factors and receptors. In general, such orphan proteins are difficult and cumbersome to clone. These orphan factors and receptors can be beneficially employed, however, in cell culture techniques in research and industrial settings, in studies of cell physiology and metabolism, in studies of relationships among factors, receptors, and cell lineages, and for therapeutic intervention in animals, including humans.

As used herein, the terms "secretory leader sequence" and "signal (or signal peptide) sequence" are used interchangeably to denote a DNA sequence encoding a signal or secretory peptide. Signal sequences are also called leader sequences, prepro sequences and pre sequences. A secretory leader is an amino acid sequence that is involved in directing secretion of a mature polypeptide or protein from a cell. More specifically, a secretory leader directs translocation of a polypeptide or protein across the endoplasmic reticulum (the entry to the secretory pathway). Secretory peptides are characterized by a core of hydrophobic amino acids and are typically (but not exclusively) found at the amino termini of newly synthesized proteins. Very often the secretory peptide is cleaved from the mature protein during secretion in one or more cleavage events. Such secretory peptides contain processing sites that allow cleavage of the secretory peptides from the mature proteins as they pass through the secretory pathway. The term "amino-terminal signal sequence" is used herein to denote a DNA sequence encoding signal peptide that occurs at the amino terminus of a protein.

As used herein, the term "leader-less protein" denotes a secreted structural protein wherein the protein's native, functional signal peptide (or "leader") has been eliminated. In one technique for obtaining a leader-less protein, the native signal peptide is eliminated through genetic manipulation of the nucleotide sequence encoding the natural signal peptide.

The term "receptor" is used herein to denote a cell-associated protein that binds to a bioactive molecule (i.e., a ligand, which term includes hormones and growth factors) and mediates the effect of the ligand on the cell. Receptors are characterized by a multi-domain structure comprising a ligand-binding domain and an effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

Receptors are classified into families and superfamilies on the basis of conserved structural features. It is generally believed that under selective pressure for organisms to acquire new biological functions, new receptor family members arose from duplication of existing receptor genes leading to the existence of multi-gene families.

Two of the most well-known receptor superfamilies are the cytokine receptor superfamily and the seven transmembrane domain (7-TMD) receptor superfamily. Table 1 provides a partial listing of members of these three receptor superfamilies.

Many cytokine receptors can be placed into one of five related families on the basis of certain structural features. All five families are characterized by the presence of an extracellular ligand binding domain and an intracellular domain that are separated by a single transmembrane sequence. Cytokine receptor structure has been reviewed by Urdal, *Ann. Reports Med. Chem.* 26:221–28, 1991 and Cosman, *Cytokine* 5:95–106, 1993.

The 7-TMD receptors are a functionally diverse group encoded by a large gene superfamily. Two characteristic features of this receptor superfamily are the presence of seven helical transmembrane domains and a cytoplasmic domain, the latter of which is believed to be responsible for coupling the receptor to G proteins. This superfamily has been reviewed by Lameh et al., *Pharm Res.* 7:1213–21, 1990; Hargrave, *Curr. Opin. Struct. Biol.* 1:575–81, 1991; and Probst et al., *DNA and Cell Biol.* 11:1–20, 1992.

TABLE 1

Cytokine superfamily
Immunoglobulin family
   CSF-1 receptor
   MGF receptor
   IL-1 receptor
   PDGF receptor
Hybrid family
   G-CSF receptor
   IL-6 receptor
Hematopoietin family
   erythropoietin receptor
   IL-2 receptor β-subunit
   IL-3 receptor
   IL-4 receptor
   IL-5 receptor IL-7 receptor
IL-9 receptor
GM-CSF receptor α-subunit
GM-CSF receptor β-subunit
IL-6 receptor
growth hormone receptor
TNF receptor
　TNF (p80) receptor
　TNF (p60) receptor
Other
　IL-2 receptor α-subunit
　IFN-γ receptor
7-TMD superfamily
　m1 muscarinic acetylcholine receptor
　m2 muscarinic acetylcholine receptor
　m3 muscarinic acetylcholine receptor
　m4 muscarinic acetylcholine receptor
　m5 muscarinic acetylcholine receptor
　beta 1 adrenergic receptor
　beta 2 adrenergic receptor
　beta 3 adrenergic receptor
　alpha 1 adrenergic receptor
　alpha 2A adrenergic receptor
　alpha 2B adrenergic receptor
　alpha 2-C4 adrenergic receptor
　dopamine D1 receptor
　dopamine D2 receptor
　dopamine D3 receptor
　dopamine D4 receptor
　dopamine D5 receptor
　thrombin receptor
　thromboxane receptor
　FSH receptor
　cannabinoid receptor
　gonadotropin receptor
　thyrotropin receptor
　calcitonin receptor
　parathyroid hormone receptor Receptors are also classified on the basis of common functions. Table 2 presents a listing of receptor families grouped according to function. Each tyrosine kinase family is represented in Table 2 by a prototypical receptor. See Ullrich et al., *Nature* 308:418–25, 1984; Ullrich et al., *Nature* 313:756–61, 1985; Yaden et al., *Nature* 323:226–32, 1986; Hirai et al., *Science* 238:1717–20, 1987; Sanchez-Madrid et al., *Proc. Natl. Acad. Sci. U.S.A.* 79:7489–93, 1982; Takeichi, *Science* 251:1451–55, 1991; Takeichi, *Ann. Rev. Biochem.* 59:237–52, 1990; and Cunningham et al., *Science* 236:799–806, 1987.

TABLE 2

Tyrosine kinase receptors
EGF receptor
insulin receptor
PDGF receptor
EPH receptor
Cell adhesion receptors
leukointegrins
cadherin receptors
immunoglobulin-like receptors Many orphan receptors have been identified, and it is anticipated that many more will be found as knowledge of the molecular biology of cells increases. Known orphan receptors include the nuclear receptors COUP-TF1/EAR3, COUP-TF2/ARP-1, EAR-1, EAR-2, TR-2, PPAR1, HNF-4, ERR-1, ERR-2, NGFI-B/Nur77, ELP/SF-1 and, prior to studies disclosed herein, Mpl (see reviews by Parker, ibid. and Power et al., ibid.). A large number of orphan receptors have been identified in the EPH family (Hirai et al., ibid., incorporated herein by reference). HER3 and HER4 (Plowman et al., *Proc. Natl. Acad. Sci. U.S.A.* 90:1746–50, 1993, incorporated herein by reference) are orphan receptors in the epidermal growth factor receptor family, which may be overexpressed in a number of carcinomas. ILA is a newly identified member of the human nerve growth factor/tumor necrosis factor receptor family (Schwarz et al., *Gene* 134:295–98, 1993, incorporated herein by reference). An orphan receptor in the insulin receptor family, designated insulin receptor-related receptor (IRRR) is disclosed by Shier et al. (*J. Biol. Chem.* 264: 14606–08, 1989, which is incorporated herein by reference). IRRR is a transmembrane tyrosine kinase. In addition, a number of orphan tyrosine kinase-type receptors have been found in Drosophila (reviewed by Perrimon, *Curr. Opin. Cell Biol.* 6:260–66, 1994, which is incorporated herein by reference). Drosophila orphan receptors are of interest because they present the opportunity for genetic, as well as biochemical, analysis. Identification of Drosophila ligands followed by cloning by homology provides a method for obtaining human or other animal counterparts to the Drosophila ligands.

As used herein, the term "growth factor" denotes a polypeptide that stimulates proliferation of a cell, the activity of which is mediated by a cell-surface receptor. Examples of growth factors include the interleukins and colony stimulating factors.

As used herein, the term "expression vector" denotes a DNA molecule, either single- or double-stranded, linear or circular, that comprises a gene of interest operably linked to other DNA sequences that provide for its expression and maintenance in a host cell. Expression vectors may be plasmid or virus-derived, or may contain both plasmid and viral elements. In general, a DNA segment encoding a structural gene is joined to expression control sequences in an expression vector that may comprise, in addition, one or more origins of replication, one or more selectable markers, enhancers, splice signals or other elements. In a preferred embodiment of the present invention, the structural gene encodes a leader-less protein, preferably a growth factor receptor that is normally transported to the cell surface. In a particularly preferred embodiment, the leader-less structural protein is Mpl. The expression vector is inserted into the host cell using conventional methods. Methods for constructing expression vectors and transfecting cultured cells are known in the art. See, for example, Levinson et al., U.S. Pat. No. 4,713,339; Hagen et al., U.S. Pat. No. 4,784,950; Palmiter et al., U.S. Pat. No. 4,579,821 and Ringold, U.S. Pat. No. 4,656,134, which are incorporated herein by reference in their entirety. For a description of genetic engineering, factor-dependent cell lines, and cell culture techniques, see U.S. Pat. No. 5,541,085, which is incorporated herein in its entirety.

In general, standard cloning of unknown proteins involves developing a specific, functional assay to detect such protein, then assaying the biological activity of putative bioactive proteins or expression products of large cDNA libraries. However, these standard approaches to cloning novel factors and proteins have certain limitations: (1) the sensitivity and/or specificity of the functional assay may not be sufficient to permit detection of the unknown protein; (2) the unknown protein of interest must be present or expressed at a detectable level; (3) proteases, inhibitors and antagonists present in complex mixtures can mask the presence of the desired protein; (4) if the unknown protein is large and/or non-contiguous domains are required for its biological activity, the bioassay may not detect expression of a protein product that is less than full-length; (5) a functional assay for the novel factor or protein may not exist; and (6) the inability to clone a protein whose function is unknown.

Using the methods of the claimed invention, these drawbacks of standard cloning approaches, as applied to novel, unknown proteins, may be avoided.

A. Enrichment of 5' Signal Sequence cDNAs

The claimed signal trap cloning method involves enrichment of N-terminal (i.e., 5') coding sequences. Within the present invention, a full length, oligo-dT-primed cDNA library is 5' terminus-labeled with biotin through ligation with a biotinylated 5' PCR linker (also denoted "5' PCR primer").

Biotin is used herein as an exemplary member of a complementary/anti-complementary pair. Such complementary/anti-complementary pairs include receptor/ligand pairs, antibody/antigen (or hapten or epitope) pairs, sense/antisense polynucleotide pairs, a biotin/avidin (or streptavidin) pair and the like. For use within the present invention, the complementary/anti-complementary pair preferably has a binding affinity of $<10^{-9}M$.

The biotinylated 5' PCR linker contains a predetermined restriction site. In a preferred embodiment, the biotinylated 5' PCR linker contains an EcoRI site. The biotinylated cDNA is divided into pools, and each pool is cut with one of a panel of "4-cutter" restriction enzymes to generate small cDNA fragments. As used herein, the term "4-cutter restriction enzyme" means a restriction enzyme having a 4 base pair (4 bp) recognition site. On average, a 4-cutter restriction enzyme will cut a sequence of cDNA approximately every 250 bp. Numerous 4-cutter restriction enzymes are commercially available; a list of representative 4-cutter restriction enzymes is provided in Table 3.

TABLE 3

| 4-Cutter Restriction Enzymes and Recognition Sequences | | | |
|---|---|---|---|
| AluI | AG↓CT | RSAI | GT↓AC |
| DdeI | C↓TNAG | BstUI | CG↓CG |
| HinfI | G↓ANTC | HinPII | G↓CGC |
| TaqI | T↓CGA | HPAII | C↓CGG |
| HaeIII | GG↓CC | MseI | T↓TAA |
| Sau3A | ↓GATC | NlaIII | CATG↓ |
| AciI | C↓CGC | Tsp509I | ↓AATT |
| BfaI | C↓TAG | | |

"N" denotes any nucleotide

Biotinylated 5' terminal fragments are isolated using avidin that has been immobilized on a solid phase matrix. In a preferred embodiment, streptavidin-conjugated magnetic beads are used. The solid phase matrix containing avidin-captured 5' fragments is washed, and a 3' PCR linker is ligated to the fragments by means of the 4-cutter-generated cohesive ends of the fragment. In a preferred embodiment, the 3' PCR linker contains a predetermined restriction site, with an XhoI restriction site particularly preferred. The captured cDNA fragments are then removed from the solid phase matrix using restriction sites present on the 5' and 3' PCR linkers. This 5' enriched cDNA preparation is then used for signal sequence library construction. Alternatively, if the amount of captured cDNA is limited, it can be amplified by PCR using the 5' and 3' PCR primers prior to signal sequence library construction. Other nucleic acid amplification methods are known in the art (see, for example, Kwoh et al., *Proc. Natl. Acad. Sci. U.S.A.* 86:1173–77, 1989; Van Gelder et al., *Proc. Natl. Acad. Sci. U.S.A.* 87:1663–67, 1990; Fahy et al., *PCR Meth. Appl.* 1:25–33, 1991; and Kievitis et al., *J. Virol. Meth.* 35:273–86, 1991), and are suitable for use in this regard.

The claimed methods for enrichment of 5' signal sequence cDNAs provide the following advantages. First, depending on the amount of starting cDNA, this technique can be amenable to direct cloning or PCR-amplification/cloning of the 5' cDNA fragments. Second, digestion of full length sequences with a panel of 4-cutter restriction enzymes allows more control over fragment generation than random shear methods. Third, avidin capture of biotinylated 5' cDNA fragments ensures efficient enrichment of native N-terminal coding cDNAs. Fourth, by identifying the 4-cutter pool from which the cDNA fragments were obtained, specific 4-cutter-generated ends of the 5' enriched cDNA fragments can be ligated to an appropriate 3' linker with high efficiency. Fifth, the known 5' and 3' linkers attached to the cDNA fragments permit directional cloning into an appropriate vector. Sixth, if PCR amplification of captured cDNA is used, a permanent copy of the captured cDNA remains on the solid phase matrix. This permanent copy can be used in the future as a PCR template.

B. Detection/Selection of Signal Sequence cDNAs

As noted above, the immunostaining method used by Tashiro et al. for signal sequence trap cloning is cumbersome and lacks any selection mechanism. The claimed invention provides two detection/selection improvements that are advantageously used to clone signal sequence cDNAs.

For both methods, putative signal sequence cDNAs are introduced in a directed, specific manner into an expression vector that contains a coding sequence for a leader-less protein. This expression vector preparation is introduced into an appropriate host cell, forming an expression host cell. The expression host cell is cultured under conditions that support cell growth, and that permit cell surface expression of the leader-less protein when it is operably linked to its own signal sequence. When a functional signal sequence cDNA has been properly inserted into the expression vector, the previously leader-less protein (the "marker protein") can be expressed and directed to the surface of the expression host cell.

In the first method, the expression host cells are cultured for a time sufficient to enable detection of the marker protein on the cell surface. These cells are then combined with a reagent that (i) specifically binds to the marker protein, and (ii) is labeled with a detectable tag. Suitable reagents in this regard include antibodies, ligands, soluble receptors and the like. Detectable tags suitable for use include fluorescent, fluorescence quenching, dye and magnetic tags and the like. In addition, any tag that modifies the light scattering properties of the target to which it is bound is suitable for use herein. Within the present invention, a preferred reagent is a fluorescent tagged anti-marker protein antibody. The expression host cells are then sorted according to the presence or absence of detectable tag/reagent bound at the cell surface. Thus, in one step, expression host cells containing a functional signal sequence are readily segregated from those in which a functional signal sequence is lacking. In a preferred embodiment, an automated machine that permits single cell examination (for instance, a flow cytometer) is used to detect and sort/select expression host cells that express the marker protein at the cell surface. In a particularly preferred embodiment, a fluorescence-activated flow cytometer is used to segregate cells containing a functional signal sequence.

In the second method, a biological selection procedure is employed. In a prototype of this method, the leader-less protein encoded by the expression vector is a cytokine receptor or a growth factor receptor. When such receptor is introduced into a factor-dependent cell line (the "parental cell"), cell surface expression of the receptor permits cell proliferation (i) in the presence of the receptor's corresponding cytokine or growth factor, and (ii) in the absence of the factor(s) upon which the starting cell-line is dependent.

Accordingly, an expression vector preparation containing a leader-less protein and putative signal sequence cDNAs (see discussion of first method, above) is introduced into a factor-dependent parental host cell, forming a factor-dependent expression host cell. This factor-dependent expression host cell is cultured in the presence of the factor necessary for parental cell proliferation. In addition, the selected culture conditions will otherwise support factor-dependent expression host cell growth, and will permit cell surface expression of the leader-less protein when it is operably linked to its own signal sequence.

The factor-dependent expression host cells are cultured for a period sufficient to allow expression of the leader-less protein at the surface of cells that contain a functional signal sequence. Thereafter, the factor-dependent expression host cells are cultured under selection conditions: (i) in the absence of the factor necessary for parental cell proliferation, and (ii) in the presence of a molecule that will enable proliferation of cells that express the (formerly leader-less) protein at the cell surface. Upon continued culturing under these selection conditions, only cells that contain a functional signal sequence will survive.

Secretion leaders that are cloned, identified, and isolated using the disclosed methods can provide alternative and/or superior secretion leaders for use as research and production tools. Prokaryotic, yeast, fungal, insect or mammalian secretion leaders can be discovered through use of the described techniques. For instance, these secretion peptides may display a range of secretion efficiencies and specificities. As new expression host cells are available, these methods can be used to identify one or more secretion leaders that can be used in creating suitable expression vectors for expression of heterologous proteins in such host cells. When using relatively uncharacterized expression host cells, methods for identifying secretion leaders in the absence of a relevant bioassay can be particularly valuable tools.

A more detailed description of these methods is provided below.

1. Automated Selection of Functional Signal Sequence cDNAs

In a prototypical procedure, the first selection method uses automated cell sorting to isolate clones that express a detectable cell surface protein due to insertion of a functional signal sequence. In one embodiment, a complex mixture of nucleic acid fragments containing putative signal sequence cDNAs are directionally cloned into an appropriate vector upstream of a nucleotide sequence encoding a leader-less structural protein that, when linked to its endogenous leader (or signal sequence), is normally transported to the cell surface.

An exemplary structural protein (i.e., "marker protein") in this regard is thrombopoietin receptor (i.e., Mpl). Other receptors that may be suitable for use as a marker protein within the present invention include (1) receptors that "stand alone" (i.e., function/enable cell proliferation without the presence of additional, distinct subunits); and (2) receptors that require the presence of one or more such subunits that are encoded by a separate, unrelated gene for the host cell's proliferative response.

Examples of receptors requiring at least one additional subunit include IL-6, IL-3 and IL-4. A skilled artisan will recognize that proteins that are: (1) normally linked to an endogenous signal peptide; (2) expressed at the cell surface; and (3) capable of being stably bound and detected by a tagged reagent can be used as marker or structural proteins herein. A skilled artisan will further recognize that selected marker proteins may accept longer segments of N-terminal modification than others.

An exemplary selection vector contains a leader-less Mpl coding region. The leader-less Mpl cDNA was isolated by reverse transcriptase polymerase chain reaction (PCR) using standard techniques (see, for instance, U.S. Pat. No. 5,541, 085). As shown, this exemplary expression vector represents a set of 3 vectors that are identical except that, at the junction between the putative signal sequence and the Mpl coding sequence, the indicated Xho site has 3 frames available ("Xho(1, 2, 3 frames)") with respect to Mpl. The PCR primer located at this junction (3' primer) is designed so that it will not amplify the endogenous structural protein signal sequence. In addition, the PCR primer located at the junction upstream of the putative signal sequence (the 5' primer) is also designed so that it will not amplify the endogenous structural protein signal sequence. Thus, if no functional signal sequence cDNA is inserted in the EcoRI-Xho site, structural protein will not be expressed and transported to the cell surface. Genomic DNA or cDNA from BaF3 as may be used as a template. Genomic DNA is easier and faster to isolate, but cDNA is less complex and may be more artifact-free.

A library of putative signal sequence cDNAs inserted in an appropriate vector is introduced into host cells capable of expressing the structural protein of interest. Exemplary host cells include prokaryotic and eukaryotic cells, and more particularly, mammalian, yeast and insect cells. After introducing the expression vector into host cells and culturing the resultant expression host cells, these cells are combined with a tagged, detectable reagent. This tagged reagent is capable of binding a marker protein expressed at the cell surface. A preferred tagged reagent is a fluorescent-labeled antibody, with a monoclonal fluorescein isothiocyanate (FITC)-labeled anti-Mpl antibody particularly preferred.

If a functional signal sequence has been properly inserted into the expression vector, the marker protein will be expressed at the cell surface. An appropriate, detectably tagged reagent is combined with cultured expression host cells, and, after an appropriate period of time, the cells are separated from unbound tagged reagent. When these "washed" cells are subjected to an appropriate cell sorting procedure, only expression host cells containing a functional signal sequence will be detected and selected. For example, fluorescence-activated cell sorting can provide a quick, one-step, automated segregation of cells that contain a functional signal sequence from those that do not.

From the detected and sorted (selected) population of expression host cells, signal sequence cDNAs of interest may be isolated clonally or en masse. For clonal isolation, expression host cells that contain a functional signal sequence can be cloned and expanded, and/or the signal sequence cDNA may be used as a probe or as a PCR primer to recover sufficient amounts of the cDNA of interest for sequencing. In the en masse approach, the totality of signal sequence DNAs can be isolated from the total population of expression host cells containing a functional signal sequence. A total signal trap cDNA preparation is then obtained using nucleotide sequence amplification techniques, such as PCR.

After the mixture of cDNAs of interest is amplified, in one alternative, the recovered cDNA can be recloned into the expression vector for additional cycles of enrichment. After enrichment, individual cDNA clones can be isolated for sequencing. In another alternative, the mixture of amplified cDNAs can be used as a sense primer to generate full-length cDNAs of interest. This library of full-length cDNAs can then be subjected to clonal isolation to obtain a single cDNA. Each cloned cDNA can then be sequenced, expressed and characterized.

Any signal sequence that does not exhibit identity or significant homology to known signal sequences contained within available sequence data bases (e.g., Genbank, EMBL) represents a fragment of a cDNA that encodes a novel secreted protein. Thus, such new signal sequence can be used as a hybridization probe or as a PCR primer to isolate its endogenous, full-length structural coding sequence. Using this technique, novel secreted proteins, such as cytokines, growth factors, and transmembrane proteins, may be cloned and identified without the need for previous development of a bioassay system specific for such protein.

2. Biological Selection

Another method for selecting functional signal sequences involves a biological selection scheme. Such biological selection protocol is an attractive alternative to automated cell sorting/selection, since it does not require an expensive, specialized piece of equipment (for instance, a flow cytometer), and can be conveniently performed in most laboratory settings.

In an exemplary protocol, a signal sequence cDNA library is inserted into an expression vector (as described above in Section B.1.), and this expression vector is introduced into a factor-dependent cell line. The expression vector encodes a leader-less structural protein. Structural proteins suitable for use within this biological selection method include cell surface receptors that are capable of mediating intracellular signal transduction. It is preferred that such signal transduction directly or indirectly causes stimulation of cell proliferation. Preferred structural proteins in this regard include Mpl, IL-4 receptor, EPO receptor, GM-CSF receptor and the like.

Suitable factor-dependent cell lines in this regard include growth factor-dependent myeloid and lymphoid progenitor cells. These are cells that give rise to differentiated blood cells and that are found in hematopoietic tissue, such as bone marrow, spleen and fetal liver. Myeloid and lymphoid precursors are also found in peripheral blood after treatment of an animal with cytokines. Preferred growth factor-dependent cell lines that can be transfected to express detectable receptors include BaF3 (Palacios and Steinmetz, *Cell* 41: 727–34, 1985; Mathey-Prevot et al., *Mol. Cell. Biol.* 6: 4133–35, 1986), FDC-P1 (Hapel et al., *Blood* 64: 786–90, 1984), and MO7e (Kiss et al., *Leukemia* 7: 235–40, 1993). Additional growth factor-dependent cell lines are known and available in the art and are disclosed by, for example, Greenberger et al., *Proc. Natl. Acad. Sci. U.S.A.* 80:2931–35, 1983; Dexter et al., *J. Exp. Med.* 152:1036–47, 1980; and Greenberger et al., *Virology* 105:425–35, 1980. In addition, growth factor-dependent cell lines can be established according to published methods (e.g., Greenberger et al., *Leukemia Res.* 8: 363–75, 1984; Dexter et al., in Baum et al. Eds., *Experimental Hematology Today*, 8th Ann. Mtg. Int. Soc. Exp. Hematol. 1979, 145–56, 1980).

Within the present invention, preferred factor-dependent cell lines readily take up exogenous DNA and have a known receptor subunit repertoire. One of ordinary skill in the art will recognize that certain characteristics of some factor-dependent cell lines may be used to select particular cell surface-expressed structural proteins as preferred marker elements in the selection vector to be employed. For instance, for a BaF3 host cell, leader-less IL-4, EPO and GM-CSF receptor coding regions may be substituted for the Mpl coding region of the selection vector. When combining BaF3 host cells with vector encoding a member of the tyrosine kinase receptor family, an EGF receptor structural gene is suitable, while a Tyro 3 receptor structural gene is not (see, for example, Stitt et al., *Cell* 80:661–70, 1995). In general, if a selected member of the tyrosine kinase receptor family "couples" to an appropriate accessory subunit in the proposed host cell, it is suitable for use as a marker structural gene in a selection vector described herein.

Inserted cDNA fragments that encode a functional signal sequence capable of directing Mpl to the factor-dependent expression host cell surface will confer thrombopoietin (TPO) dependency to this host cell. That is, if the factor required for parental factor-dependent cell proliferation is removed, a factor-dependent expression host cell expressing Mpl at its surface can only survive and proliferate in the presence of TPO. Thus, cDNAs encoding functional signal sequences can be selected by growing factor-dependent expression host cells in the absence of the required factor, but in the presence of TPO. In a preferred embodiment, the factor-dependent cell line is BaF3, and the required factor for parental factor-dependent cell proliferation is IL-3. Factor-dependent expression host cells that do not contain a functional signal sequence cannot express Mpl at the cell surface. Therefore, if the factor required for parental cell growth is absent, these factor-dependent expression host cells that do not contain a functional signal sequence will not survive when cultured with TPO. Functional signal sequence cDNAs of interest may be isolated clonally or en masse from the entire surviving factor-dependent expression host cell population, as described in Section B.2., above, for fluorescence activated flow cytometry-selected cells.

Both the cell sorting and biological selection methods described above permit enrichment of functional signal sequence coding regions with minimal screening.

The invention is further illustrated by the following non-limiting examples.

EXAMPLES

Example 1
Construction of Selection Vector

A selection vector system was constructed to allow the directional cloning of short Eco RI/Xho I cDNA segments encoding putative signal sequences. Briefly, plasmid pHZ-1 was linearized downstream of the MT-1 promoter at the Xho I site. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an *E. coli* origin of replication; a bacterial beta-lactamase gene; a mammalian selectable marker expression unit comprising the SV40 promoter and origin, a neomycin resistance gene and the SV40 transcription terminator.

Into the Xho I site was cloned, in the same orientation with respect to the MT-1 promoter, Xho I/Sal I cDNA fragments encoding the mature murine Mpl in each of three reading frames. The sequence encoding murine Mpl has been described by (see, for example, Skoda et al., *EMBO J.*

12:2645–53, 1993; Vigon et al., *Oncogene* 8:2607–15, 1993). Leader-less Mpl-encoding cDNAs were isolated by PCR amplification from a full length mouse Mpl cDNA template using (i) an antisense primer containing a Sal I site (GAG GAG AAG GTC GAC TCA AGG CTG CTG CCA ATA GCT TAG; Sal I site underlined; SEQ ID NO: 1); and (ii) each of three sense primers containing a Xho I site in one of three reading frames with respect to the Mpl coding sequence. The resultant plasmids were designated as pSLSV-1, pSLSV-2 and pSLSV-3, which upon digestion with Eco RI and Xho I facilitate the cloning of leader sequences.

The sequences of the cloning regions of pSLSV-1, pSLSV-2 and pSLSV-3 are shown below:

| pSLSV-1 (Frame 1): | | | | | | | |
|---|---|---|---|---|---|---|---|
| CTC | GAG | GG(T) | CAA | GAT | GTC | TTC | SEQ ID NO: 2 |
| Leu | Glu | Gly | Gln | Asp | Val | Phe | |
| pSLSV-2 (Frame 2): | | | | | | | |
| TCG | AG(T) | CAA | GAT | GTC | TTC | | SEQ ID NO: 3 |
| Ser | Ser | Gln | Asp | Val | Phe | | |
| pSLSV-3 (Frame 3): | | | | | | | |
| CGA | G(GT) | CAA | GAT | GTC | TTC | | SEQ ID NO: 4 |
| Arg | Gly | Gln | Asp | Val | Phe | | |

The underlined portions of frames 1–3 indicate a complete or partial XhoI recognition sequence. The "(T)" indicates substitution of thymine for the adenine present in the native Mpl signal peptide cleavage site.

Example 2
Fragment Size Tolerance of Selection Vectors

Various sizes of cDNA fragments encoding human GM-CSF (huGM-CSF) signal sequence, as well as encoding varying lengths of the huGM-CSF mature sequence (see, for instance, Wong et al., *Science* 228:810–15, 1985), were inserted into the Eco RI/Xho I cloning sites of pSLSV-1, -2 and -3. More specifically, the following inserts were placed in frame in the appropriate pSLSV expression vector: (1) 1–66 huGM-CSF, wherein the insert encoded the 17 amino acid signal peptide plus 49 amino acids beyond it; (2) 1–133 huGM-CSF, wherein the insert encoded the 17 amino acid signal peptide plus 116 amino acids beyond it; and (3) 1–17 huGM-CSF, wherein the insert encoded the 17 amino acid signal peptide only. Negative control inserts included: (a) 18–116 huGM-CSF, wherein the insert encoded 116 amino acids beyond the signal peptide, but did not encode a signal peptide; and (b) 18–66 huGM-CSF, wherein the insert encoded 66 amino acids beyond the signal peptide, but did not encode a signal peptide. Another negative control inserted an ATG (met) codon next to the leaderless-Mpl coding region, to show that Mpl was not secreted in the absence of a signal peptide.

These plasmids were transfected into IL-3-dependent BaF3 cells in RPMI medium using electroporation, and $10^5$ cells/ml were cultured overnight in the presence of IL-3 (5% WEHI conditioned medium). At day 1, the transfected BaF3 cells were plated in microtiter plates at 500 cells/well, and cultured in the presence of G418 and recombinant TPO (100 units/ml). G418 selects transfectants that contain the pHZ-1 plasmid (neomycin resistance). surviving clones were observed when the following DNA segments were inserted into the pHZ-1 vector: 1–66 huGM-CSF; 1–133 huGM-CSF; and 1–17 huGM-CSF. All other constructs did not produce surviving, transfected BaF3 cells. Thus, in-frame insertion of a cDNA fragment containing a functional, heterologous huGM-CSF signal sequence into the Eco RI/Xho I cloning site of pSLSV-1, -2 and/or -3 rendered a population of transfected BaF3 cells thrombopoietin growth-dependent. Further, the expression vector set tolerated insertion of additional nucleotides that encoded >100 amino acids beyond the terminus of the huGM-CSF signal peptide.

Modifications to this protocol include: (i) growing the transfectants in the presence of IL-3 for 1, 2, or 4 days before switching to TPO selection; and (ii) testing various concentrations and species of recombinant TPO. For the first, survival of TPO-dependent clones was better when the described manipulation occurred day 1 or day 2, rather than at day 4. With the second, increasing the TPO concentration may increase the sensitivity of the method, permitting more survivors to be detected.

IL-3 rescue experiments were conducted. Transfected cells were incubated as a pool overnight in the presence of IL-3. On day 1, the cells were washed and plated in microtiter plates in the presence of TPO and G418. On day 2, 4 or 7, IL-3 was added ("IL-3 rescue") to the wells. Clones were observed with day 4 and day 7 IL-3 rescue.

Example 3

Selection Vectors and Biological Selection

Following enrichment of 5' cDNA fragments by streptavidin affinity chromatography, the cDNA fragments are released from the solid phase support by digestion with Eco RI. A secretion trap library is constructed by digestion of the released cDNA with Xho I, and is directionally cloned into a vector preparation consisting of equal molar amounts of Eco RI/Xho I-digested pSLSV-1, pSLSV-2 and pSLSV-3. Alternatively, if the amounts of captured cDNA fragments are limiting, they can be amplified by PCR using the 5' and 3' PCR primers prior to cloning into the selection vector. Following transfection of the secretion library into IL-3-dependent BaF3 cells, the cells are cultured in the presence of G418 and thrombopoietin, but in the absence of IL-3. Mpl, when expressed on the surface of BaF3 cells, couples into the proliferative pathway, such that in the presence of its ligand thrombopoietin, the host cell exhibits growth independence from other exogenous growth factors (e.g., IL-3). From the surviving cells, functional secretion sequences are isolated using RT-PCR from cell mRNA or PCR from cell genomic DNA, employing a 5' sense primer to the vector sequence and a 3' antisense primer spanning the vector Xho I site. PCR isolation of secretion leader sequences may be performed using isolated clones of cells, or using a pool of cells in an en masse PCR reaction. Secretion leader sequences may be cloned into the selection vector for a further round of enrichment in BaF3 cells.

Full-length cDNA from which the secretion sequence originated can be isolated by PCR from a oligo-dT-primed cDNA library, employing a 5' sense primer synthesized to the secretion sequence and a 3' antisense primer directed to an anchor sequence attached to the oligo-dT cDNA synthesis primer. Alternatively, a totality of signal sequences are used as sense primer to amplify full-length cDNA en masse.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for selecting DNA molecules comprising the 5' end of a gene comprising:

preparing a plurality of DNA molecules each comprising the 5' end of a gene, wherein said 5' ends are linked to a first member of a complementary/anti-complementary pair, thereby forming labeled 5' ends;

cleaving said DNA molecules with a restriction endonuclease, thereby forming DNA fragments having labeled 5' ends;

exposing the DNA fragments to an opposite member of the complementary/anti-complementary pair, whereby DNA fragments having labeled 5' ends are bound to the opposite member; and isolating DNA fragments from the complementary/anti-complementary pair.

2. The method of claim 1 wherein the complementary/anti-complementary pair is selected from the group consisting of a biotin/avidin pair, a receptor/ligand pair, an antibody/epitope pair, and a sense/antisense polynucleotide pair.

3. The method of claim 1 wherein the first member of the complementary/anti-complementary pair is biotin and the opposite member is avidin.

4. The method of claim 1 wherein the opposite member of the complementary/anti-complementary pair is immobilized on a solid phase matrix.

5. The method of claim 4 wherein the solid phase matrix is a magnetic bead.

6. The method of claim 1 wherein the restriction endonuclease is a 4-cutter restriction enzyme.

7. The method of claim 1 further comprising, after the step of isolating DNA fragments, the additional steps of:

joining the DNA fragments to a DNA segment encoding a structural protein, thereby forming a DNA fusion, wherein the DNA fusion is contained within an expression vector and operably linked to other DNA elements required for expression of the DNA fusion in a host cell;

introducing the expression vector into a host cell, thereby forming an expression host cell; and culturing the expression host cell, whereby the DNA fusion is expressed.

8. The method of claim 7 wherein the structural protein is a growth factor receptor.

9. The method of claim 7 wherein the structural protein is Mpl.

10. The method of claim 7 wherein the expression vector is selected from the group consisting of pSLSV-1, pSLSV-2, pSLSV-3 and combinations thereof.

11. The method of claim 7 wherein the host cell is selected from the group consisting of a BaF3 cell line, a Chinese hamster ovary cell line, a baby hamster kidney cell line, an FDC-P1 cell line, and an MO7e cell line.

12. The method of claim 7 wherein the host cell is a BaF3 cell.

13. The method of claim 7 further comprising, after the step of culturing the expression host cell, the additional steps of:

combining the expression host cell with a tagged reagent under conditions whereby the expression host cell is intact and the tagged reagent binds to the structural protein encoded by the DNA segment; and isolating expression host cells that bind the tagged reagent.

14. The method of claim 13 wherein the tagged reagent is a fluorescent-labeled antibody.

15. The method of claim 14 wherein the step of isolating is performed using a fluorescence-activated cell sorter.

16. A method for selecting a DNA molecule comprising a 5' functional signal sequence, the method comprising:

a) preparing a plurality of DNA molecules each comprising the 5' end of a gene;

b) linking the 5' ends to a first member of a complementary/anti-complementary pair to form labeled 5' ends;

c) cleaving the DNA molecules with a restriction endonuclease to form DNA fragments having labeled 5' ends;

d) exposing the DNA fragments to an opposite member of the complementary/anti-complementary pair, whereby DNA fragments having labeled 5' ends are bound to the opposite member;

e) isolating DNA fragments having 5' ends from the complementary/anticomplementary pair;

f) joining the DNA fragments having 5' ends to a DNA segment encoding a leader-less growth factor receptor to form a DNA fusion protein, the DNA fusion protein being contained within an expression vector and being operably linked to other DNA elements required for expression of the DNA fusion protein in a host cell;

g) introducing the expression vector into a host cell to form an expression host cell; and h) culturing the expression host cell in the presence of a growth factor ligand which binds to said growth factor receptor, whereby proliferation of the expression host cell is dependent upon cell surface expression of said DNA fusion protein containing a 5' functional signal sequence.

17. The method of claim 16 wherein the host cell is a factor-dependent host cell.

18. The method of claim 17 wherein the factor-dependent host cell is selected from the group consisting of a BaF3 cell line, an FDC-P1 cell line, and an MO7e cell line.

19. The method of claim 17 wherein the factor-dependent host cell is a BaF3 cell line.

20. The method of claim 16 wherein the growth factor receptor is selected from the group consisting of Mpl, IL-4 receptor, EPO receptor, and GM-CSF receptor.

21. The method of claim 16, wherein the complementary/anti-complementary pair is selected from the group consisting of a biotin/avidin pair, a receptor/ligand pair, an antibody/epitope pair and a sense/antisense polynucleotide pair.

22. The method of claim 16, wherein the first member of the complementary/anti-complementary pair is biotin and the opposite member is avidin.

* * * * *